(12) United States Patent
Ede et al.

(10) Patent No.: US 7,401,713 B2
(45) Date of Patent: Jul. 22, 2008

(54) PACK CONTAINING MEDICAMENT AND DISPENSING DEVICE

(75) Inventors: Andrew John Ede, Cambridge (GB); Douglas Ivan Jennings, Herts (GB)

(73) Assignee: Meridica Limited, Melbourn, Hertfordshire (GB)

( * ) Notice: Subject to any disclaimer, the term of this patent is extended or adjusted under 35 U.S.C. 154(b) by 391 days.

(21) Appl. No.: 10/486,713

(22) PCT Filed: Aug. 16, 2002

(86) PCT No.: PCT/GB02/03807
§ 371 (c)(1),
(2), (4) Date: Apr. 26, 2004

(87) PCT Pub. No.: WO03/015857
PCT Pub. Date: Feb. 27, 2003

(65) Prior Publication Data
US 2004/0206773 A1      Oct. 21, 2004

(30) Foreign Application Priority Data
Aug. 16, 2001    (GB)    .................... 0120018.7

(51) Int. Cl.
*B67D 5/00* (2006.01)
(52) U.S. Cl. .................... 222/83; 128/203.21
(58) Field of Classification Search .................... 222/83, 222/83.5, 80, 85, 88; 206/532, 469, 531; 220/359.1; 128/203.15, 203.12, 203.21
See application file for complete search history.

(56) References Cited

U.S. PATENT DOCUMENTS

| 4,158,411 | A | | 6/1979 | Hall et al. | |
| 4,357,192 | A | * | 11/1982 | Moser | 156/252 |
| 5,924,417 | A | | 7/1999 | Braithwaite | |
| 5,954,204 | A | * | 9/1999 | Grabowski | 206/531 |
| 6,082,356 | A | | 7/2000 | Stradella | |
| 6,443,307 | B1 | * | 9/2002 | Burridge | 206/532 |

FOREIGN PATENT DOCUMENTS

| DE | 44 00 083 A1 | 7/1995 |
| DE | 44 00 084 A1 | 7/1995 |
| GB | 2 264 237 A | 8/1993 |
| GB | 2 292 557 A | 2/1996 |
| WO | WO 97/40876 A2 | 11/1997 |
| WO | WO 01/17595 A1 | 3/2001 |
| WO | WO 01/30430 A1 | 5/2001 |
| WO | WO 01/45634 A1 | 6/2001 |
| WO | WO 01/85097 A2 | 11/2001 |
| WO | WO 02/00279 A1 | 1/2002 |

* cited by examiner

*Primary Examiner*—Lien T Ngo
(74) *Attorney, Agent, or Firm*—Foley & Lardner LLP

(57) ABSTRACT

A pack containing medicament, the pack including a base having first and second opposing faces, at least one recess being formed in the first face, a foil secured to the first face so as to form with the at least one recess a sealed compartment for housing medicament and a substantially rigid member housed in the compartment extending generally from the second face to the first face such that the member can be pushed from the second face so as to rupture the foil outwardly of the compartment at the first face without compressing the medicament and a dispensing device for use with or including such a pack having an actuator for pushing the member from the second face so as to rupture the foil outwardly of the compartment at the first place.

7 Claims, 4 Drawing Sheets

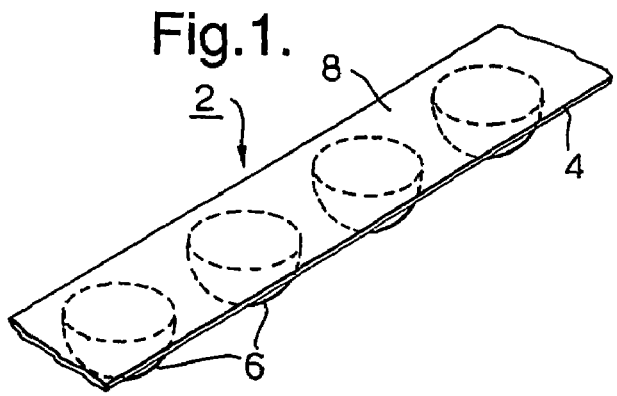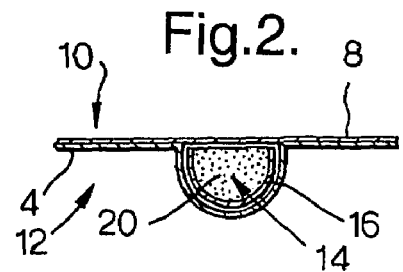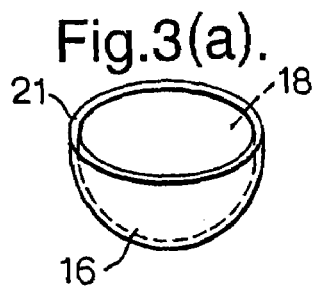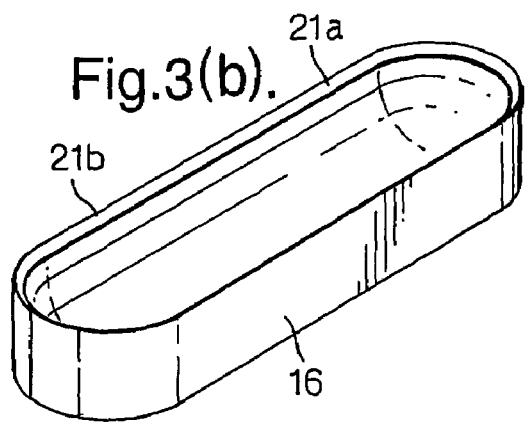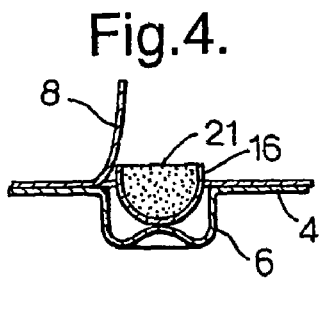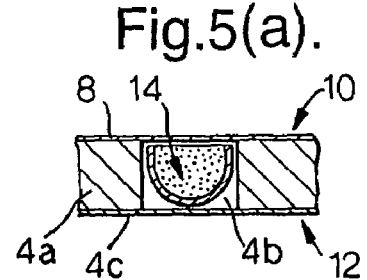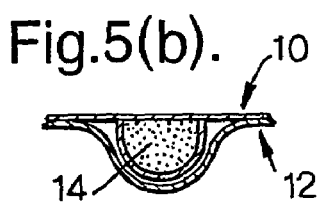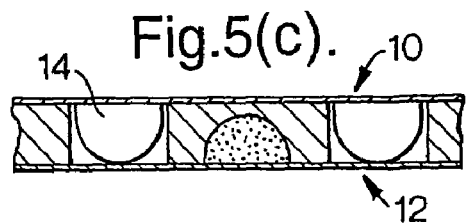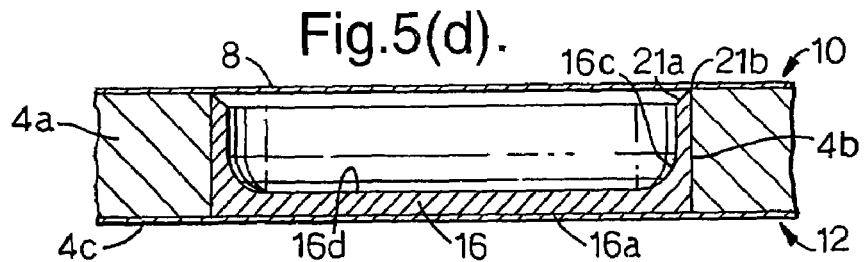

PACK CONTAINING MEDICAMENT AND DISPENSING DEVICE

The present invention relates to a pack containing medicament and a dispensing device, either for use with the pack or including the pack.

In the field of dry powder drug delivery, it is known to provide a reservoir of dry powder and a dosing mechanism which draws a predetermined quantity of powder, i.e. a unit dose, from the reservoir. Although this allows a large number of doses to be carried in a relatively small volume, it is very difficult to meter the required quantity of medicament accurately and repeatably. Furthermore, the powder, when stored or metered, may become compressed and agglomerated to varying degrees.

As an alternative approach, it is also known to pre-meter individual unit doses into respective compartments of a pack, such that individual compartments may be opened and individual unit doses of medicament may be dispensed.

The compartments may be formed as so called blister packs in which preformed pockets or blisters are sealed with a lidding foil.

In order to open the compartments, the lidding foil may be pierced using a sharp edge to puncture the foil, so as to allow air to flow into and out of the compartments. In doing so, the foil is pressed into the compartment, thereby preventing the compartment from being fully opened, such that it is not fully or repeatably emptied of the powder.

It is also possible to peel the foil away from the base so as to open the compartments. However, the dispensing devices used to do this are more complex, since it is necessary to control the tension of the lidding foil and to control accurately the amount of unpeel such that only one compartment is opened at a time. Additionally, the compartments must be spaced out so as to simplify the positional control. This increases the size of the blister pack and the dispensing device.

It is an object of the present invention to provide a system of packing medicament such that individual unit doses of the medicament may be dispensed whilst avoiding the problems identified above.

According to the present invention, there is provided a pack containing medicament, the pack having first and second opposing faces and including:

a base having at least one recess formed at the first face;

a lidding sheet secured to the base at the first face so as to form with the at least one recess a sealed compartment for housing medicament; and a substantially rigid member housed in the compartment extending generally from the second face to the first face such that the member can be pushed from the second face so as to rupture the lidding sheet outwardly of the compartment at the first face without compressing the medicament.

Thus, a member separate from the base and the lidding sheet is provided to rupture the lidding sheet outwardly. In this way, it is not necessary to provide a complex unpeeling mechanism and the compartments of the pack may be spaced closely with respect to one another. Furthermore, the lidding sheet may be opened outwardly of the recesses such that the recesses become fully open to air flow and allow complete removal of powder from the compartments. By providing the rigid member within the compartment to rupture the lidding sheet, pressure on the second face to cause rupturing of the first face does not compress or agglomerate the medicament within the pack. This is clearly of significant advantage when the medicament is in a dry powder form, for instance for inhalation into the lungs or the nasal cavities.

The member may be of any appropriate form extending between the first and second faces and allowing it to be pushed from the second face to rupture the foil without compressing the medicament. However, the member is preferably generally cup-shaped, an open portion of the member facing the lidding sheet and the medicament being contained in the member.

In this way, the medicament may be retained within the cylinder and one end of the cylinder may be pushed at the second face from outside the recess so as to cause the other end of the cylinder to rupture the lidding sheet.

The bottom of the cup-shaped member may be pushed at the second face so that the edges surrounding the open portion rupture the lidding sheet. Since the medicament is contained in the member itself, there is no danger of the medicament being compressed and, as the cup pushes through the lidding sheet, it exposes the inside of the cup and allows dispensing of the medicament therefrom. The medicament is, in effect, lifted out of the recess, thereby making it easier to be removed.

Preferably, the member is generally oval in a cross-section generally parallel with the first and second faces. However, it could also be generally cylindrical with an axis generally perpendicular to the first and second faces.

Preferably, at the first face, walls of the base defining the at least one recess have a shape and spacing matching a peripheral wall of the member.

In this way, the member fits closely within the recess and is guided by the walls of the base defining the recess. When the member is pushed outwardly through the lidding sheet, the peripheral wall of the member engages the lidding sheet at the periphery of the recess so that the lidding sheet is opened to give the maximum possible opening.

Preferably, at least part of the peripheral wall includes a chamfer on an end surface facing said first face, the chamfer forming a cutting edge for rupturing the foil at the outer periphery of the member.

For structural integrity of the member, outer walls of the member have to have a reasonable thickness. Although this thickness might still allow the upper ends of the walls to rupture the lidding sheet, the precise location of the rupturing becomes less certain. By providing chamfered/bevelled or angled upper ends to the walls such that they angle upwardly and outwardly towards the periphery and lidding sheet, it can be assured that the rupturing occurs neatly at the periphery.

Preferably, a portion of the member facing the lidding sheet is shaped so as to rupture the lidding sheet in a predetermined pattern.

Thus, it is possible to ensure that the way in which the compartments are exposed is approximately the same each time a compartment is opened. This allows any dispenser device to be arranged in such a way as to provide repeatably the most efficient way of dispensing the medicament. For instance, in the case of dry powder, the dispenser device can be arranged to provide an air flow appropriate for the pattern in which the lidding sheet is ruptured.

The portion may include one or more protrusions extending beyond the general surface (for instance the lip of the cup shape as mentioned above) of the member. The protrusions may extend from surfaces proximate the first face or the second face.

Alternatively, surfaces of the member facing the lidding sheet may be shaped to achieve the desired effect, for instance with some parts of the member contacting the lidding sheet ahead of others.

Preferably, the lidding sheet is arranged so as to rupture in a predetermined pattern.

The lidding sheet may be formed with a weakened section adjacent the compartment such that the lidding sheet ruptures at the weakened section.

In this way, similarly to as discussed above, it becomes possible to expose the medicament in a repeatable manner thereby facilitating the construction of a dispensing device and allowing improved efficiency in dispensing medicament from the recess.

The weakened section may run around part of the periphery of the compartment and/or across it, for instance on a diameter The weakened section may be formed by at least one of varying the thickness and material properties of the lidding sheet.

In particular, it might be formed by scoring the material, embrittelling the material (for instance by work hardening or heat treatment) or strengthening the non-tearing portions (for instance by coating).

The lidding sheet may be secured to the base with a particular pattern. In particular, the sealing between the lidding sheet and the base need not exist at all portions. If no seal is provided at particular portions adjacent the periphery of a recess the sheet will tend to rupture where the seal is present, thereby resulting in one or more flaps hinged from the portions where the seal does not exist.

Preferably, the lidding sheet is foil, for instance made of a metal such as aluminium.

The base may be formed in a known construction, such as from a moulded metal and plastics material laminate.

Alternatively, the base may comprise a plate with a secondary lidding sheet secured over the second face, the plate defining at least one through hole, the at least one through hole forming, together with the secondary lidding sheet, said at least one recess.

Preferably, a surface of the member at the second face is generally co-planar with the second face.

Thus, the bottom surface of the member adjacent the secondary lidding sheet is generally co-planar with the second face of the base. In this way, gaps need not be formed between the member and the secondary lidding sheet and there is less chance of accidentally rupturing the secondary lidding sheet. On the other hand, the bottom surface of the member is easily and securely engaged via the secondary lidding sheet when the secondary lidding sheet (and hence the member) are pushed from the second face.

Preferably, the member includes inner surfaces defining a volume for containing the medicament, the inner surfaces curving without discontinuities between side surfaces and a base surface so as to allow an air flow within the volume to remove contained medicament.

Thus, whereas the outer surfaces of the member may include side surfaces which follow the inner surface of the recess (whatever shape that might be) and have a flat bottom surface, the inner surfaces of the member may be sculpted and curved to provide a good flow of air to remove any medicament, particularly powder.

As mentioned above, the medicament may be in the form of dry powder for instance for inhalation to the lungs or dispensing to nasal cavities.

Preferably, the pack includes a plurality of the compartments.

In this way, the pack includes a plurality of unit doses of medicament which may be dispensed individually one by one by rupturing the lidding sheet of the respective compartments.

According to the present invention, there is also provided a dispensing device for use with or including a pack as defined above, the device including:

a dispenser outlet; and an actuator for pushing said member from the second face so as to rupture the lidding sheet outwardly of the compartment at the first face and release the medicament for dispensing through the dispenser outlet.

Thus, unlike dispensing devices using peeling, a relatively simple opening or actuating mechanism may be provided. This mechanism need not be any more complex than mechanisms for piercing the foil inwardly and yet provides the advantages discussed above of repeatably and completely opening the compartments to dispense the medicament.

Preferably, the dispensing device includes a support positioned adjacent the compartment proximate the first face so as to control rupturing of the lidding sheet as the actuator pushes the member.

In this way, the support provides additional support to sealing of the lidding sheet, for instance by pressing the lidding sheet onto the first face. This prevents the lidding sheet from rupturing or tearing and/or prevents the bond between the lidding sheet and the base from breaking where the support is positioned and, hence, further controls rupturing of the lidding sheet.

The support may extend generally around the periphery of the compartment so as to support the lidding sheet where it is secured to the base of the first face.

Preferably, the support includes a peripheral wall which is in line with the periphery of the compartment, a portion of the peripheral wall extending to meet the lidding sheet and the remainder of the peripheral wall having a recess adjacent the lidding sheet such that the lidding sheet ruptures along said portion.

By providing the recess adjacent the lidding sheet, movement of the outer peripheral walls of the member against the lidding sheet tends to deflect the lidding sheet in the area of the recess rather than rupture it. In this way, the lidding sheet is ruptured in a defined manner along the defined portion of the peripheral wall. It will remain attached in the area of the remainder of the peripheral wall such that it is not dispensed with the housed medicament.

Alternatively, the position of the support relative to the centre of the compartment may be varied around the periphery of the compartment so as to encourage the lidding sheet to rupture in a predetermined manner and form one or more outwardly extending flaps of lidding sheet hinged at one or more predetermined positions.

By varying whether support is provided adjacent the lidding sheet close to or away from the periphery of the compartment, it is possible to encourage the lidding sheet to rupture at predetermined positions around the periphery.

The dispensing device may be provided with an indexing mechanism for successively moving each of a plurality of compartments to a position adjacent the actuator and support, where applicable, for dispensing the contents of the respective compartments.

In this way, where a plurality of compartments are provided in a pack, the pack may be moved to position the compartments as necessary. Alternatively, where a single compartment is provided in individual packs, the indexing mechanism can move respective packs into position.

The present invention is of particular advantage when used in a dry powder inhaler, for instance for dispensing dry powder to the lungs or nasal cavities.

The invention will be more clearly understood from the following description, given by way of example only, with reference to the accompanying drawings, in which:

FIG. 1 illustrates a blister pack embodying the present invention;

FIG. 2 illustrates a cross-section through the blister pack of FIG. 1;

FIG. 3(a) illustrates the member of FIG. 2 and FIG. 3(b) illustrates an alternative member;

FIG. 4 illustrates a cross-section corresponding to FIG. 2;

FIG. 5(a) illustrates a alternative pack embodying the present invention;

FIG. 5(b) illustrates a cross-section of a blister similar to those of FIG. 1;

FIG. 5(c) illustrates a pack similar to that of FIG. 5(a);

FIG. 5(d) illustrates an alternative to FIG. 5(a);

Figure 14A:
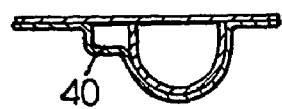
Figure 15A:
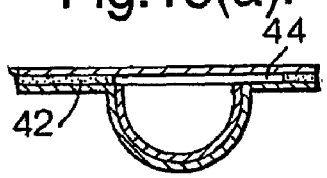
Figure 16:
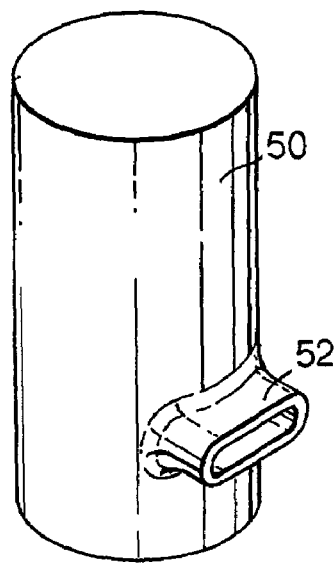
Figure 18:
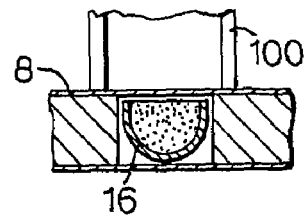
Figure 19:
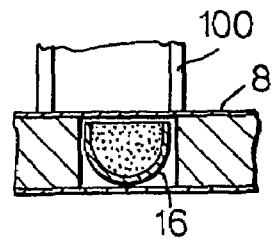
Figure 17:
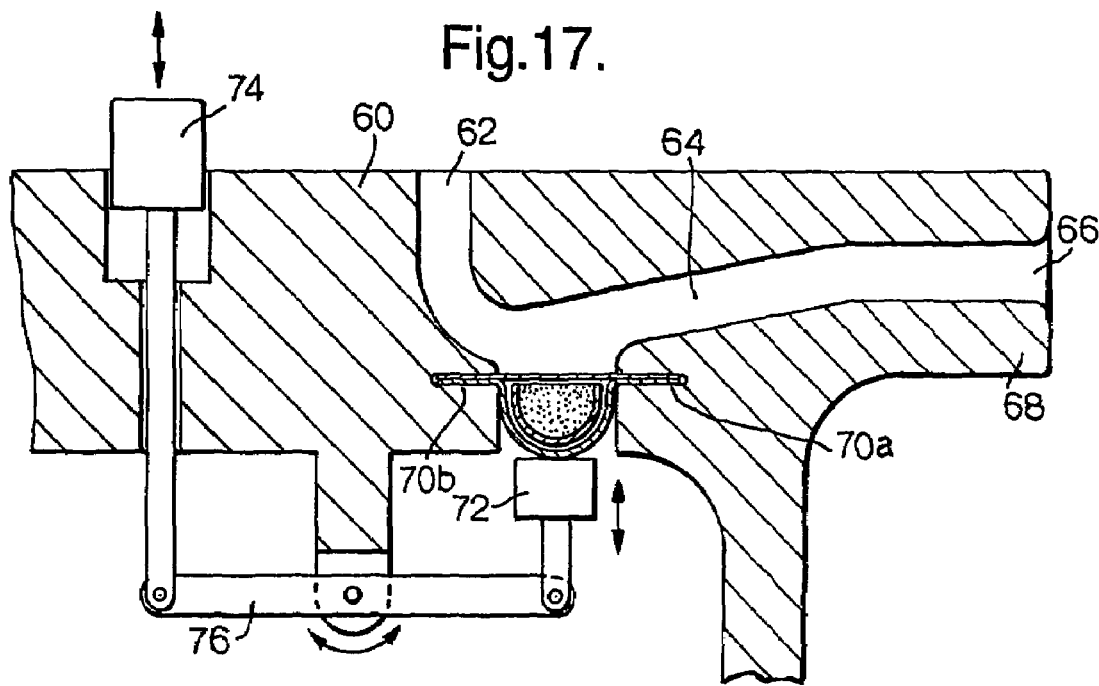

FIGS. 13(a) to (d) illustrate various patterns for lidding sheets;

FIGS. 14(a) and (b) illustrate a shaped recess;

FIGS. 15(a) and (b) securing a lidding sheet to a base with a predetermined pattern;

FIG. 16 illustrates a dispensing device embodying the present invention;

FIG. 17 illustrates an actuation mechanism;

FIG. 18 illustrates a support for use in a dispensing device;

FIG. 19 illustrates an alternative support; and

Figure 20:
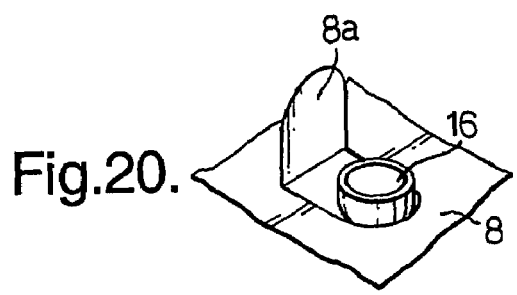
Figure 21A:
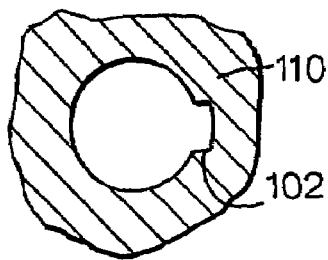
Figure 22:
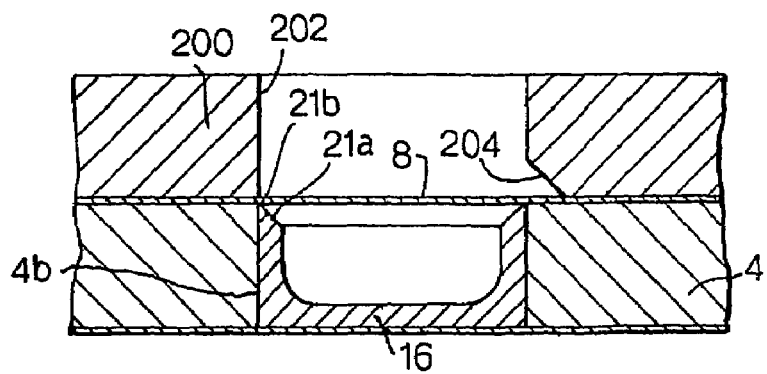

FIG. 20 illustrates a foil ruptured using the support of FIG. 19;

FIGS. 21(a), (b) and (c) illustrate rupturing of a lidding sheet using a support similar to that of FIG. 19; and FIG. 22 illustrates an alternative support.

In general, blister packs for holding unit doses of medicament are known. Individual packs including respective unit doses can be provided or a single pack may be provided with a plurality of individual unit doses.

FIG. 1 illustrates a blister pack embodying the present invention and arranged in the form of a tape having a plurality of blisters arranged along the length of the tape as an elongate array.

The blister pack 2 includes a base 4 in which a plurality of recesses 6 are provided. A lidding sheet 8, such as a foil, for instance made of aluminium, is secured to a first surface (the uppermost surface as illustrated in FIG. 1) of the base 4 so as to form with the recesses 6 compartments for housing unit doses of medicament, such as tablets or, in the preferred embodiment, dry powder. The lidding sheet may also be a metal foil laminated with a plastics material or coated with any appropriate material.

The foil 8 may be secured to the base 4 in any appropriate manner, such as by means of adhesive, welding, heat sealing etc. Furthermore, for moisture sensitive medicaments, the foil 8 and base 4 are manufactured from materials which resist moisture. For instance, the foil 8 may be aluminum foil and the base 4 may be a laminated metal and plastics material combination, for instance a metal coated with plastic or a plastic having a metal coating.

It should be appreciated that the shape and size of the recesses 6 and, hence, the compartments, is not essential to the invention. In a particular preferred embodiment, the recesses are oval in plan view, for instance having an overall length of 8 mm, a width of 2.5 mm and semi-circular ends having diameters of 2.5 mm.

Recesses and compartments may be sized and shaped according to the particular application of the pack. Similarly, the arrangement or pattern of the recesses in the base is not essential to the invention and other arrays, such as rectangular or staggered arrays may be used.

The dimensions of the recess are chosen to be compatible with the preferred manufacturing route. One preferred manufacturing route is cold forming the recess from a sheet material. This approach may be used where the sheet material can be plastically deformed sufficiently to create the recess without the sheet material rupturing or pin holing. A suitable material for this would be aluminium foil laminated on both sides with a suitable laquer to provide the required functional performance for forming a container for the medicament. Thus, one surface would have an adhesure laquer to which the lidding foil would be sealed and the other surface would have one or more lacquers whose function could be selected for: protection of the metal foil from corrosion, strengthening during forming, decorative appearance etc.

In addition to lacquers which are typically printed, the foil may be laminated with one or more polymer sheet materials to provide significant mechanical strengthening to the metal foil. A wide range of aluminium foil laminates are produced designed to meet specific packaging requirements.

The function of the aluminium layer in the laminate is to prevent water vapour diffusing through the polymer material into the recesses. Typically, thicknesses are in the range 10 microns to 100 microns for the aluminium layer where preventing moisture ingress is of primary importance.

FIG. 2 illustrates a cross-section through the blister pack of FIG. 1 along a line passing through a recess 6.

The pack 4 can be considered as having a first face 10 which, in FIG. 2, faces upwardly, and a second opposite face 12 which, in FIG. 2, faces downwardly. The recess 6 is formed in the first face 10 and the foil 8 is sealed with the base 4 at a surface along the first face so as to form a sealed compartment 14.

Within the sealed compartment 14, there is a member 16.

For the illustrated embodiment, the member 16 is cup-shaped and an example of a suitable member 16 is illustrated schematically in FIGS. 3(a) and (b).

The member 16 extends within the compartment 14 from the first face 10 towards the second face 12 and defines an internal volume 18 in which the medicament 20 is provided.

As illustrated in FIG. 4, by pushing on the member 16 from the second face 12 outside the recess 6, it is possible to push an upper edge 20 of the member 16 against the foil 8 so as to rupture the foil 8 and expose the compartment 14.

The flat top 21 of the cup pushes against the lidding foil over the circumference adjacent to the sealed area surrounding the pocket. The high stress level induced in the foil causes the foil to rupture at the edge but the actual point of rupture around the circumference is not controlled.

The thickness of base material, for instance, the aluminium of a laminate, can be selected to ensure that the recess can be deformed by a mechanism for pushing the member to rupture the lidding foil without requiring excessive force whilst providing sufficient thickness of material to ensure that the material does not split or pin hole during the forming of the recess.

By providing the member 16 as a relatively rigid member extending between the first and second surfaces within the recess 6, it is possible to rupture the foil 8 without compressing the housed medicament. Of course, it is not essential that the member be cup-shaped. A generally cylindrical member could be provided and, by pressing the member from its edges at the second surface, it could also be pressed through the foil 8 without compressing the housed medicament. Other such shapes are also possible.

The cup-shape is particularly advantageous in that, as it is pushed through the foil 8, it also carries the medicament with it in the same direction such that the medicament may be removed from the internal volume 18 of the cup-shape with ease. In particular, the cup effectively lifts the medicament up out of the recess 6 to a more exposed position.

It is also advantageous for the cup-shaped member to have a rounded bottom when the medicament is dry powder because the rounded bottom makes it easier for a flow of air to remove all of the powder. The bottom may be generally hemispherical or similar.

Where the member 16 is cup-shaped so as to house the medicament in its internal volume 18, it is, of course, preferable that the shape and size of the member 16 follows the internal shape and size of the recess 6. Tis minimises any wastage of volume within the recess 6.

Suitable materials for the members 16 include polymers, metals, such as aluminium, and hard gelatine.

FIG. 5(*a*) illustrates an embodiment of the present invention similar to that of FIG. 2, but with an alternative construction for the base 4.

As illustrated, the base 4 is made up of a plate 4*a* extending from the first face 10 to the second face 12, a through hole 4*b* through the plate 4*a* and a secondary lidding sheet 4*c* sealing with the plate 4*a* along the second face 12. As illustrated, the through hole 4*b* sealed with the secondary lidding sheet 4*c* forms a compartment 14.

The secondary lidding sheet 4*c* may be constructed in the same way as the lidding sheet 8, i.e. as a foil, for instance of aluminium. The plate 4*a* may be constructed from a range of materials, for instance moulded plastic, such as polypropylene. Polyethylene is preferred, ideally high density polyethylene. It is also possible to use stamped metal which could be lacquer coated after forming or provided with any other suitable surface treatment. It is proposed to use bare aluminium.

In this embodiment, the member 16 can again be pushed from the second face 12 so as to rupture the foil 8 at the first face 10. Of course, it may be that the secondary foil 4*c* will be inwardly ruptured or torn when the member 16 is pushed towards the foil 8. However, where the member 16 itself contains the medicament 20, this is not important.

The advantage of this arrangement is that it allows recess shapes which are not achievable by cold forming aluminium foil. Specific features which can be obtained using this approach include eliminating the gap between member and the recess into which drug could be trapped (see FIG. 5(*b*)), and allowing desiccant to be included between recesses underneath the foil (see FIG. 5(*c*)).

The member 16 provides two primary functions. It provides a hard cutting edge which is able to pierce the foil 8 from the inside and it provides a means by which this edge can be pressed from outside the compartment, in particular from the second face. In this way, the compartment may be opened in a more simple manner than for a peelable foil, the compartment is fully opened so as to allow powder (where that is the medicament) to be fully evacuated, it protects medicaments, such as therapeutic powders, from being compressed and the compartments can be closely spaced so as to increase packing density.

FIG. 5(*d*) illustrates a cross-section through the oval member of FIG. 3(*b*) located in a base as described above. The member 16 fits in the through hole 4*b* of the plate 4*a* with a bottom surface 16*a* adjacent the secondary lidding sheet 4*c*. Indeed, the bottom surface 16*a* may be co-planar with the bottom of the plate 4*a* and, hence, the secondary lidding sheet 4*c*. The end surfaces of the peripheral walls of the member 16 facing the lidding sheet 8 are formed with chamfers 21*a* to be described below. The top edge of the chamfers 21*a* sits level with the upper surface of the plate 4*a* and hence the lidding sheet 8. Inner surfaces 16*c* of the member 16 which provide the required volume for housing medicament extend between side surfaces and a base surface 16*d* without discontinuity so as to allow a good air flow within the volume to remove any medicament.

In a preferred embodiment, as mentioned above, the member 16 and, hence, the through hole 4*b* has an overall length of 8 mm and a width of 2.5 mm. Preferably, the plate 4*a* is 3 mm thick and the base surface 16*d* is positioned 2.7 mm below the lidding foil 8.

In order to improve the reliability and repeatability of the rupturing of the foil 8, the surface or edge of the member 16 which contacts the inside of the foil 8 may have a predetermined shape or form.

As illustrated in the oval embodiment of FIG. 3(*b*), the top edge or surface to face the lidding sheet includes an angled section or chamfer 21*a* which forms a cutting edge 21*b* at the outer periphery. When the member 16 is pushed against the inside of the foil is it cut effectively by the outer edge 21*b*.

Figure 6:
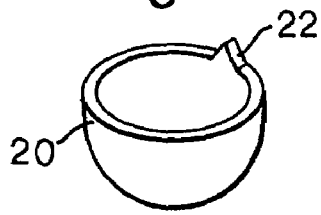
FIGS. 6 to 12 illustrates various members for use in packs according to the invention.

As illustrated in FIG. 6, the member may include a pointed feature 22 extending above the flat surface 20 such that only the point 22 contacts the foil when it is pushed upwards. The high local pressure causes the foil to rupture at this point. The continued upward motion of the member applies pressure around the circumference causing the tear to extend around the circumference to the point at which the foil can fold back along a line diametrically opposite the point allowing the member to exit the pocket.

Figure 7:
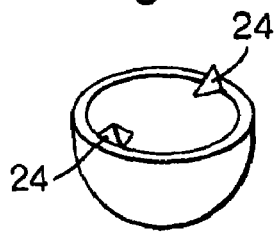

As illustrated in FIG. 7, the member may include two triangular raised points 24 diametrically opposed. The shape of the triangular point is chosen to create a tear in the foil, as the member is pushed out of the pocket, along the diameters joining the points. This produces an initial diametric split of the foil. As the member moves out, circumferential tears form from the points until the foil folds back into two semicircular flaps.

This reduces the motion of the member necessary to raise its edges above the folded back foil edge.

Figure 8:
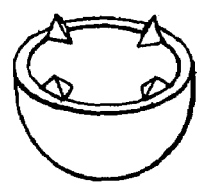

The member may include any number of similar raised points. For instance, FIG. 8 illustrates the use of 4 points to form quarter circle flaps with no circumferential tearing.

Figure 9:
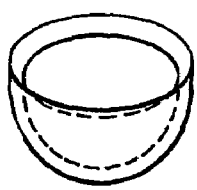

As illustrated in FIG. 9, a circularly symmetric cup shaped member may be provided where the top edge has a chisel edge to increase the pressure loading on the foil as the cup is pressed forward. The foil may start to tear at any point around the circumference with the tear propagating around the circumference to form a single flap as with the arrangement of FIG. 6. The flat top of the cup is advantageous for filling the member with a controlled amount of medicament. In particular, it allows over filling of the cup and then scraping of excess off with a blade.

Figure 10A:
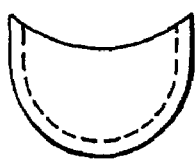
Figure 10B:
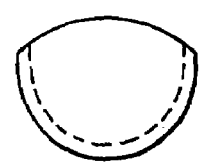

As a variation, the top edge may be curved in one plane rather than flat. This is illustrated in FIGS. 10(*a*) and (*b*). This provides two raised areas on the circumference which increases the tearing force compared to the arrangement of FIG. 9 but still allows excess drug to be scraped off by a blade during filling.

Figure 11A:
Figure 11B:
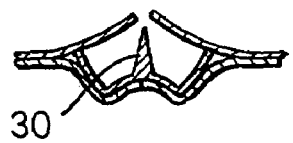
Figure 11C:

As illustrated in FIGS. 11(*a*), (*b*) and (*c*), the member may include a centrally located pointed cruciform shape 30 attached to the base of the member. The base of the member is designed to deform when it is pressed in the centre whilst being prevented from moving by the lidding foil contacting the outer edges of the member. As the base deforms, the central point the foil causing it to rupture in a plurality of radial tears. To enhance the initiation of a tear, the deformation of the base of the member may take the form of a bistable motion. Once the lidding foil has been torn, the continued motion of the member pushes the flaps of the foil away from the opening.

Figure 12:
Figure 13A:
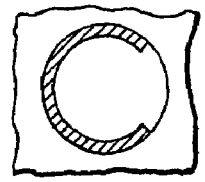
Figure 13B:
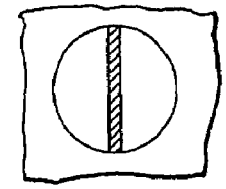
Figure 13C:
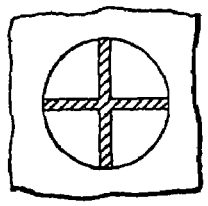
Figure 13D:
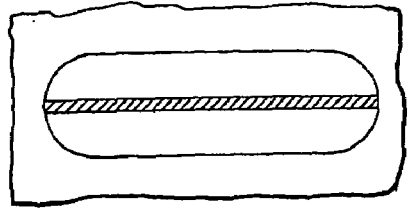

Finally, as illustrated in FIG. 12, a cup shaped member may be provided with a bevelled edge where the leading edge initiates the rupturing of the foil.

In order to increase the reliability and repeatability of rupturing of the foil 8, the foil 8 itself may include features which encourage rupturing in particular portions of the foil. For instance, the material properties and/or thickness of the foil may be varied in regions to encourage rupturing in those regions. Thus, in particular, by way of example, the material could be scored so as the thin material along the line or embrittled, for instance by work hardening or heat treatment, to cause a reduction of the mechanical properties of the foil along a line. Alternatively, non-tearing parts of the lidding sheet could be strengthened, for instance by printing, spraying or plating the sheet on the upper surface with a reinforcing lacquer/laminate in all portions of the sheet except the weakened area.

FIGS. 13(*a*) to (*d*) illustrates examples of appropriate patterns for the weakened sections.

FIGS. 13(*a*) to (*c*) are illustrated for circular compartments.

According to FIG. 13(*a*) a weakened section is provided around all except one portion of the circumference of the recess or compartment. This results in a single-flap hinge. According to FIG. 13(*b*), a diametric weakened section is provided so as to give rise to two flaps. According to the FIG. 13(*c*) arrangement, two perpendicular diametric weakened sections are provided so as to give rise to four flaps.

FIG. 13(*d*) illustrates an arrangement equivalent to that of FIG. 13(*b*), but for an elongate recess. A weakened section is provided across the centre of the recess in a longitudinal direction so as to give rise to two flaps of reduced height.

Figure 14B:
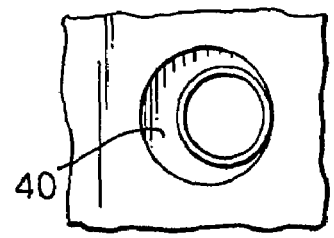

FIGS. 14(*a*) and (*b*) illustrate an alternative arrangement for controlling the tear of the lidding sheet during opening of the compartment.

In particular, as illustrated by the cross-section of FIG. 14(*a*), the recess is provided with a shelf section 40. This shelf section 40 or, indeed, any other appropriate shaping of the recess is provided to cause the member 16 to be located within the recess at a predetermined position. In particular, the member 16 is located off-centre and to one side of the recess. The stress in the lidding sheet is highest where the pushing edge of the member 16 is closest to the edge of the recess. Hence, the lidding sheet ruptures from this point.

It is also possible to control the tearing of the lidding sheet by means of shaping appropriately the bonding area between the lidding sheet and the base.

Figure 15B:
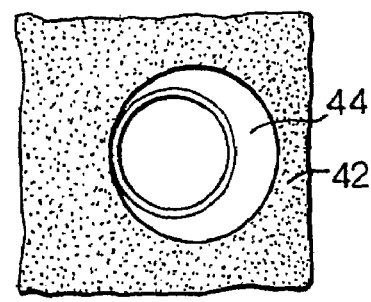

As illustrated in FIGS. 15(*a*) and (*b*), a bond 42 between the lidding sheet and the base need not be provided right up to the edge of the recess. Hence, a non-bonded region 44 may be provided at predetermined areas around the recess.

As illustrated in FIG. 15(*b*) the lidding sheet is only bonded right to the edge of the recess at one point around the recess. As the member is pushed against the lidding foil, the stress is highest at the point where the bonding occurs right at the edge of the recess. Hence, the lidding sheet will rupture at this point.

FIG. 16 illustrates a dispensing device for use with a pack as described above. It includes a dispenser outlet 52 through which unit doses of medicament are dispensed. In a preferred embodiment, where the medicament is dry powder, the dispensing device 50 may be an inhaler for providing unit doses of dry powder for inhalation to the lungs or nasal cavities.

The dispensing device 50 is suitable for accommodating a pack as described above. In particular, it is arranged to receive a pack such that a compartment can be opened by pushing the member 16 as described above.

An example of a suitable actuation mechanism is illustrated in FIG. 17.

A housing 60 of the dispensing device is formed with an air inlet 62 feeding a channel 64 with an outlet 66 in the dispenser outlet 68. As illustrated, the housing is provided with a shaped portion for holding a pack adjacent the channel 64. In the illustrated embodiment, the pack is of the form of the blister pack illustrated in FIG. 2. However, the dispensing device might just as easily be adapted to hold any other form of pack, such as that described with reference to FIGS. 5(*a*), (*c*) and (*d*). In the illustrated embodiment receiving channels 70*a* and 70*b* are provided for receiving either edge of the blister pack.

The actuating mechanism includes a bursting component 72 adjacent the lower or second face of the pack. The bursting component 72 may be moved in the direction of the first face, i.e. upwardly as illustrated, so as to push the member 16 of the pack through the lidding sheet in the manner described above.

The bursting component 72 may be operated in any known or convenient manner. However, in the illustrated embodiment, a button 74 is provided externally of the housing 60. By depressing the button 74, a cantilever 76 is rotated so as to operate the bursting component 72.

The embodiment illustrated in FIG. 17 may be used with individual blisters or with elongate strips as illustrated in FIG. 1. In the case of the strips, indexing may be achieved by any known or convenient manner. For instance, the strip may be unwound from one roll and rolled into another roll.

Similar arrangements may be provided for any form of pack. Exact positioning for the packs may be achieved by locating the packs by means of their recesses extending from the second face or by any other distinguishing features formed on the pack.

As a preferred feature, the actuation mechanism is provided with a support 100.

This is illustrated schematically in FIG. 18.

The support 100 is positioned adjacent the foil 8 on the first surface 10 of a pack. As the actuation mechanism operates to push the member 16 through the foil 8, the support 100 engages with a portion of the foil 8 surrounding the compartment and supports the pack. Where the pack and foil 8 is pushed against the support 100, the foil 8 is held securely against the base 4 such that it will not tear or rupture. By positioning the support 100 around the compartment with an appropriate spacing from the centre, it is possible to prevent the foil 8 from rupturing in certain regions and, hence, encouraging it to rupture in other regions.

FIGS. 19 and 20 illustrate how a support which is offset to one side, the left side as illustrated in the figures, will cause the foil to remain attached at that side and, hence, form a flap 8*a*.

Figure 21B:
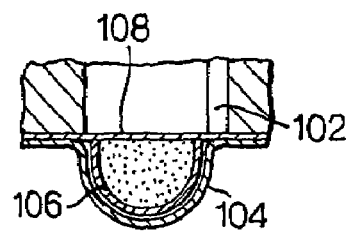
Figure 21C:
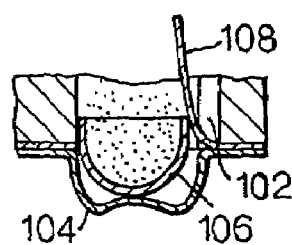

A particular example of such a support is illustrated in FIGS. 21(*a*), (*b*) and (*c*).

The support 110 above the periphery of the pocket has a short section 102 at a larger radius than the recess 104. As the member 106 is pushed through the foil 108 the adhesive bond at this side is insufficient to hold the lidding foil flat, reducing the stress at this point and ensuring that the tear initiates away from this region and propagates around the periphery away from this section. This causes the flap to be hinged about this section and provides a location for the flap out of the airflow removing the powder from the recess.

In a preferred embodiment, the support is provided as a plate 200 which is positioned on top of and against the lidding sheet 8. The plate 200 includes a peripheral wall 202 which is in line with the walls of the base 4 defining the recess or compartment. In this way, when the member 16 is pushed outwardly through the lidding sheet 8, the external peripheral surface of the member 16 continues to be guided by the peripheral wall 202 of the plate 200. As illustrated, part of the peripheral wall 202 extends all of the way down to the lidding sheet 8 so as to (in function at least) meet with the lidding sheet 8. On the other hand, the remainder of the peripheral wall 202 includes a recess 204 adjacent the lidding sheet. As illustrated, the recess is formed from a chamfered surface, but any other suitable surface, such as a step or radius would also suffice.

With this arrangement, the plate 200 functions similarly to the offset support described above. In particular, where the recess 204 is provided, the member 16 will tend merely to push the lidding sheet 8 away from the plate 4 rather than cut or tear it. Thus, the lidding sheet 8 will be cut at the portions where the peripheral wall 202 meets the lidding sheet 8 but will remain attached to the remainder of the lidding sheet 8 and the plate 4 where the recess 204 is positioned.

The illustrated embodiment includes the preferred feature of a chamfered edge 21a as described above. With this embodiment, when the member 16 is pushed outwardly through the lidding sheet 8, the cutting edge 21b of the chamfer 21a will act with the peripheral wall 202 (where it meets with the lidding sheet 8) in a scissor action to cut the lidding sheet 8.

The invention claimed is:

1. A dispensing device for use with a pack having first and second opposing faces and including: a base having at least one recess formed at the first face; a lidding sheet secured to the base at the first face so as to form with the at least one recess a sealed compartment for housing medicament; and a substantially rigid member housed in the compartment extending generally from the second face to the first face such that the member can be pushed from the second face so as to rupture the lidding sheet outwardly of the compartment at the first face without compressing the medicament, the device including:
   an air inlet;
   a dispenser outlet; and
   an actuator for pushing said member from the second face so as to rupture the lidding sheet outwardly of the compartment at the first face and release the medicament for dispensing through the dispenser outlet,
   wherein the device is arranged such that, in use, operation of the actuator exposes the inside of the member to allow dispensing of the medicament therefrom by a flow of air from the air inlet to the dispenser outlet.

2. A dispensing device according to claim 1 further including:
   a support positioned adjacent the compartment proximate the first face so as to control rupturing of the lidding sheet as the actuator pushes the member.

3. A dispensing device according to claim 2 wherein the support extends generally around the periphery of the compartment so as to support the lidding sheet where it is secured to the base at the first face.

4. A dispensing device according to claim 3 wherein the support includes a peripheral wall which is in line with the periphery of the compartment, a portion of the peripheral wall extending to meet the lidding sheet and the remainder of the peripheral wall having a recess adjacent the lidding sheet such that said lidding sheet ruptures along said portion and not adjacent said recess.

5. A dispensing device for use with a pack having first and second opposing faces and including: a base having at least one recess formed at the first face; a lidding sheet secured to the base at the first face so as to form with the at least one recess a sealed compartment for housing medicament; and a substantially rigid member housed in the compartment extending generally from the second face to the first face such that the member can be pushed from the second face so as to rupture the lidding sheet outwardly of the compartment at the first face without compressing the medicament, the device including:
   a dispenser outlet;
   an actuator for pushing said member from the second face so as to rupture the lidding sheet outwardly of the compartment at the first face and release the medicament for dispensing through the dispenser outlet; and
   a support positioned adjacent the compartment proximate the first face so as to control rupturing of the lidding sheet as the actuator pushes the member,
   wherein the support extends generally around the periphery of the compartment so as to support the lidding sheet where it is secured to the base at the first face, and
   wherein the position of the support relative to the centre of the compartment is varied around the periphery of the compartment so as to encourage the lidding sheet to rupture in a predetermined manner and form one or more outwardly extending flaps of lidding sheet hinged at one or more predetermined positions.

6. A dispensing device according to claim 1, including:
   an indexing mechanism for successively moving each of a plurality of compartments to a position adjacent the actuator for dispensing the contents of the respective compartments.

7. A device according to claim 1, wherein the device is configured to dispense a dry powder for lungs or nasal cavities.

* * * * *